United States Patent
Shochat et al.

(10) Patent No.: US 12,262,955 B2
(45) Date of Patent: *Apr. 1, 2025

(54) SYSTEMS AND METHODS FOR GUIDING THE INSERTION OF A MEDICAL TOOL

(71) Applicant: XACT ROBOTICS LTD., Caesarea (IL)

(72) Inventors: Moran Shochat, Zichron Yaakov (IL); Ofer Arnold, Ma'ale Tzvia (IL); Shraga Nahum Goldberg, Efrat (IL)

(73) Assignee: XACT ROBOTICS LTD., Caesarea (IL)

( * ) Notice: Subject to any disclaimer, the term of this patent is extended or adjusted under 35 U.S.C. 154(b) by 157 days.

This patent is subject to a terminal disclaimer.

(21) Appl. No.: 17/323,209

(22) Filed: May 18, 2021

(65) Prior Publication Data
US 2021/0322108 A1 Oct. 21, 2021

Related U.S. Application Data

(63) Continuation of application No. 15/759,240, filed as application No. PCT/IL2016/051013 on Sep. 11, 2016, now Pat. No. 11,039,891.
(Continued)

(51) Int. Cl.
*A61B 34/20* (2016.01)
*A61B 5/00* (2006.01)
(Continued)

(52) U.S. Cl.
CPC ............ *A61B 34/20* (2016.02); *A61B 5/055* (2013.01); *A61B 5/061* (2013.01);
(Continued)

(58) Field of Classification Search
CPC . A61B 10/02; A61B 17/3403; A61B 18/1477; A61B 2017/00119;
(Continued)

(56) References Cited

U.S. PATENT DOCUMENTS 6,245,028 B1 6/2001 Furst et al.
7,167,180 B1 1/2007 Shibolet et al.
(Continued)

FOREIGN PATENT DOCUMENTS

WO 2015132787 A1 9/2015

OTHER PUBLICATIONS

Gerwen et al, "Needle-tissue interaction forces—A survey of experimental data", Medical Engineering & Physics 34 (2012) pp. 665-680.

(Continued)

*Primary Examiner* — Michael T Rozanski
(74) *Attorney, Agent, or Firm* — The Roy Gross Law Firm, LLC; Roy Gross

(57) ABSTRACT

A system and method for controlling the insertion of a medical tool, such as a needle, into a subject's body based on measurements of an interaction parameter associated with the interaction between the tool and a bodily tissue, such as the forces exerted on the tool during insertion. The system comprises an insertion device, at least one sensor configured to measure the interaction parameter and at least one processor configured to receive sensor measurements, detect one or more predefined patterns in the sensor measurements and control an operation of at least one of the insertion device and an imaging device, upon detecting the predefined patterns. The processor may be configured to compare the actual correlation between the sensor measurements and an insertion parameter, such as insertion depth, with an expected correlation, and determine if the medical tool is following its pre-planned trajectory based on the result of that comparison.

16 Claims, 9 Drawing Sheets

Related U.S. Application Data

(60) Provisional application No. 62/283,734, filed on Sep. 10, 2015.

(51) Int. Cl.

| | | |
|---|---|---|
| *A61B 5/055* | (2006.01) | |
| *A61B 5/06* | (2006.01) | |
| *A61B 5/15* | (2006.01) | |
| *A61B 17/34* | (2006.01) | |
| *A61B 34/00* | (2016.01) | |
| A61B 6/12 | (2006.01) | |
| A61B 8/08 | (2006.01) | |
| A61B 10/02 | (2006.01) | |
| A61B 17/00 | (2006.01) | |
| A61B 18/02 | (2006.01) | |
| A61B 18/14 | (2006.01) | |
| A61B 34/10 | (2016.01) | |
| A61B 34/30 | (2016.01) | |
| A61B 90/00 | (2016.01) | |
| A61M 5/00 | (2006.01) | |
| A61N 1/00 | (2006.01) | |

(52) U.S. Cl.
CPC .... *A61B 5/15003* (2013.01); *A61B 5/150748* (2013.01); *A61B 5/6848* (2013.01); *A61B 17/3403* (2013.01); *A61B 34/76* (2016.02); A61B 5/7292 (2013.01); A61B 6/12 (2013.01); A61B 8/0841 (2013.01); A61B 10/02 (2013.01); A61B 2017/00119 (2013.01); A61B 2017/3407 (2013.01); A61B 2017/3409 (2013.01); A61B 2018/0293 (2013.01); A61B 18/1477 (2013.01); A61B 2034/107 (2016.02); A61B 2034/2063 (2016.02); A61B 2034/2065 (2016.02); A61B 2034/302 (2016.02); A61B 2090/064 (2016.02); A61B 2562/0252 (2013.01); A61M 5/00 (2013.01); A61N 1/00 (2013.01)

(58) Field of Classification Search
CPC .... A61B 2017/3407; A61B 2017/3409; A61B 2018/0293; A61B 2034/107; A61B 2034/2063; A61B 2034/2065; A61B 2034/302; A61B 2090/064; A61B 2562/0252; A61B 34/20; A61B 34/76; A61B 5/055; A61B 5/061; A61B 5/15003; A61B 5/150748; A61B 5/6848; A61B 5/7292; A61B 6/12; A61B 8/0841; A61M 5/00; A61N 1/00
See application file for complete search history.

(56) References Cited

U.S. PATENT DOCUMENTS

| | | |
|---|---|---|
| 7,822,458 B2 | 10/2010 | Webster et al. |
| 8,348,861 B2 | 1/2013 | Glozman et al. |
| 8,663,130 B2 | 3/2014 | Neubach et al. |
| 11,039,891 B2 * | 6/2021 | Shochat ............... A61B 5/6848 |
| 2002/0120188 A1 | 8/2002 | Brock et al. |
| 2010/0114288 A1 | 5/2010 | Haller et al. |
| 2012/0265051 A1 | 10/2012 | Fischer et al. |
| 2014/0142429 A1 | 5/2014 | Neubach et al. |
| 2015/0057575 A1 | 2/2015 | Tsusaka et al. |
| 2016/0249990 A1 | 9/2016 | Glozman et al. |
| 2016/0249991 A1 | 9/2016 | Glozman et al. |

OTHER PUBLICATIONS

PCT Search Report for International Application No. PCT/IL2016/051013; dated Mar. 13, 2018; 3 pp.
PCT Written Opinion for International Application No. PCT/IL2016/051013; dated Mar. 13, 2018; 4 pp.
PCT Preliminary Report for International Application No. PCT/IL2016/051013; dated Dec. 12, 2016; 5 pp.

* cited by examiner

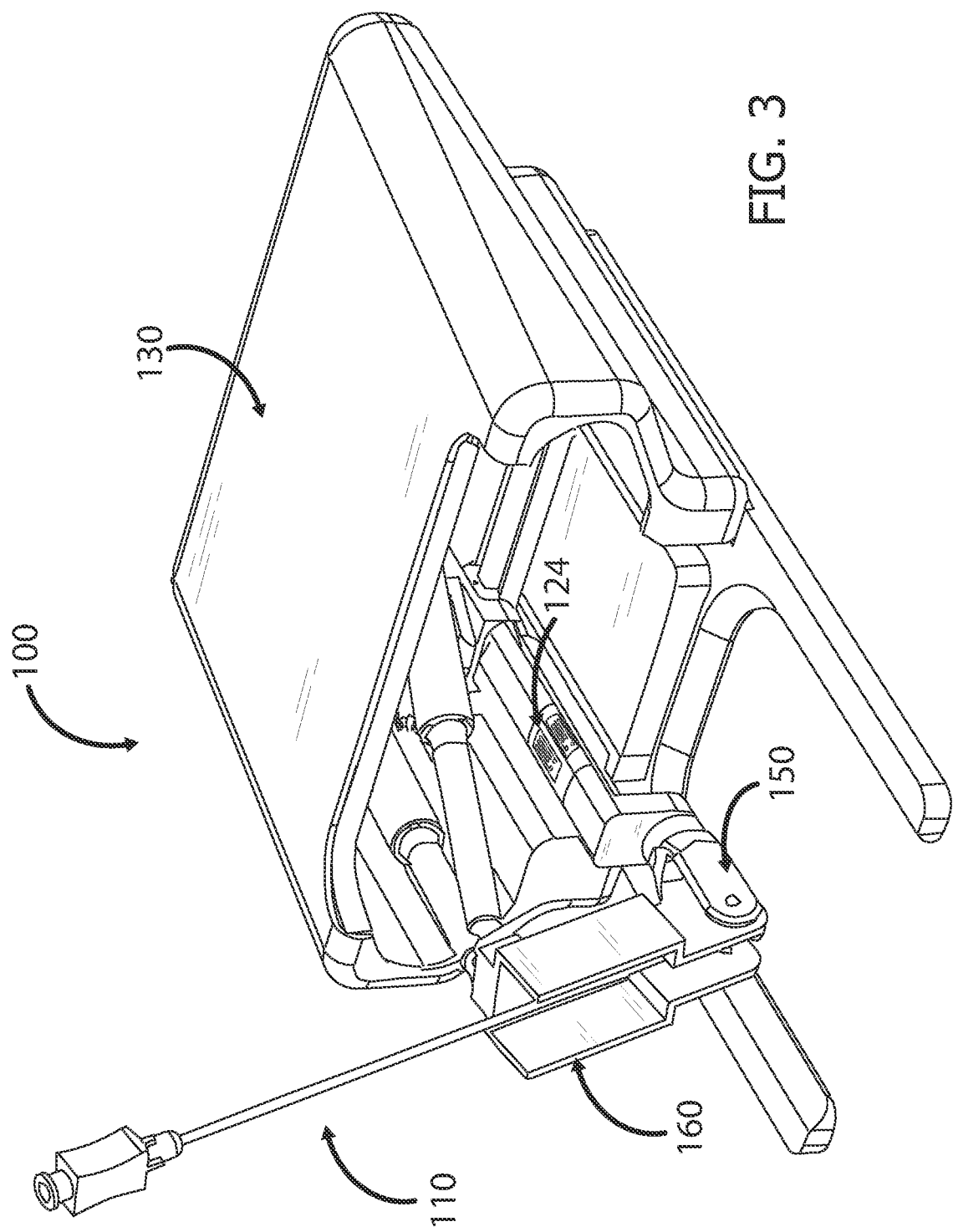

SYSTEMS AND METHODS FOR GUIDING THE INSERTION OF A MEDICAL TOOL

CROSS REFERENCE TO RELATED APPLICATIONS

This application is a Continuation of Ser. No. 15/759,240 filed on Mar. 12, 2018 which is a National Phase of PCT Patent Application No. PCT/IL2016/051013 having International filing date of Sep. 11, 2016, which claims the benefit of priority of U.S. Provisional Patent Application No. 62/283,734, filed Sep. 10, 2015, the contents of which are all incorporated herein by reference in their entirety.

FIELD OF THE INVENTION

The present invention relates to the field of automated percutaneous insertion of medical tools for diagnostic and/or therapeutic purposes, and especially to systems and methods for sensing parameters associated with tool-tissue interaction and utilizing sensor measurements to monitor and/or guide the insertion of the medical tool.

BACKGROUND

Many routine treatments employed in modern clinical practice involve percutaneous insertion of needles and catheters for biopsy and drug delivery and other diagnostic and therapeutic procedures. The aim of a needle insertion procedure is to place the tip of an appropriate needle safely and accurately in a target region, which could be a lesion, organ or vessel. Examples of treatments requiring needle insertions include vaccinations, blood/fluid sampling, regional anesthesia, tissue biopsy, catheter insertion, cryogenic ablation, electrolytic ablation, brachytherapy, neurosurgery, deep brain stimulation and various minimally invasive surgeries.

Guidance and steering of needles in soft tissue is a complicated task that requires good 3-D coordination, knowledge of the patient anatomy and a high level of experience. Therefore, robotic systems have been proposed for performing these functions. Among such systems are those described in U.S. Pat. No. 7,822,458 to Webster III et al, for "Distal bevel-tip needle control device and algorithm", U.S. Pat. No. 8,348,861 to Glozman et al, for "Controlled steering of a flexible needle" and U.S. Pat. No. 8,663,130 to Neubach et al, for "Ultrasound Guided Robot for Flexible Needle Steering".

However, a significant drawback of robotic systems is the lack of tactile feedback. In hand-held insertion devices the physicians/clinicians rely on the resistance they feel as they insert the needle into the patient's body in order tokletect reaching a tissue boundary (i.e., skin, fatty tissue, muscle, etc.) and to determine accordingly the needle's position in the patient's body. Typically, once the physician/clinician detects that a tissue boundary has been reached, the insertion procedure is paused and an image (CT, X-Ray, etc.) is taken to verify the needle's position.

The lack of tactile feedback in automated insertion systems may thus require frequent or even constant imaging (e.g., CT fluoroscopy) during the complete duration of the procedure, which results in significant radiation exposure to the patient and to the medical staff.

The physicians/clinicians further rely on the resistance they feel as they insert the needle into the patient's body in order to detect undesired contact with bones or blood vessels, for example. Thus, tactile feedback is also crucial for maintaining patient safety.

Needle-tissue interaction has been researched extensively, and it is known that there is an increase in force starting when the needle comes into contact with the tissue boundary until the tissue boundary is breached ("puncture event"). If tapered needles are used, the transition from the tapered tip of the needle to the needle shaft may also give rise to an increase in axial force. Depending on the circumstances (insertion velocity, needle type, etc.), the peak force may occur at the puncture event or at the moment the tip protrudes at the other side of the membrane and there is a transition from tip to shaft, such as is summarized in D. Gerwen et al, "Needle-tissue interaction forces—A survey of experimental data", Medical Engineering & Physics 34 (2012) pp. 665-680.

Force sensors have been previously incorporated in automated needle insertion devices, for example, in U.S. Pat. No. 6,245,028 to Furst et al, for "Needle Biopsy System", U.S. Pat. No. 8,348,861 to Glozman et al, for "Controlled Steering of a Flexible needle", U.S. Pat. No. 8,663,130 to Neubach et al, for "Ultrasound Guided Robot for Flexible Needle Steering" and U.S. Patent Application No. 2012/0265051 to Fischer et al, for "Apparatus and Method for MRI-Compatible Haptic Interface". However, in none of these cases was information from the force sensor utilized to replace imaging in monitoring and guiding needle navigation, to enable radiation exposure to both the patient and the medical staff to be significantly minimized during the needle insertion procedure.

The disclosures of each of the publications mentioned in this section and in other sections of the specification, are hereby incorporated by reference, each in its entirety.

SUMMARY

The present disclosure describes new exemplary automated systems and methods for image-guided insertion of medical tools such as needles, into a subject for diagnostic and/or therapeutic purposes, using real-time measurements of one or more parameters associated with tool-tissue interaction. Such systems and methods may be useful for monitoring, providing feedback and assisting in guiding the insertion procedure, while minimizing the exposure of the subject and the medical staff to radiation during the insertion procedure. The parameters associated with tool-tissue interaction may include, for example, tool insertion force and tissue compliance.

In some implementations, the real-time measurements provide a gating function. This means that measurements of parameter/s associated with tool-tissue interaction, such as forces exerted on the tool, including insertion forces and lateral forces, and/or tissue compliance, are used to assist in defining the optimal times/stages for initiating imaging of the region of interest, resulting in fewer images being taken throughout the insertion procedure. Images may be taken, for example, only when sensor measurements indicate that the medical tool has reached a tissue boundary or the target (e.g., tumor, lesion). Imaging may be carried out automatically by the system or the system may prompt the user to initiate imaging. The term "tissue" may include also the target to be reached, and the term "tissue boundary" may refer also to the boundary of the target.

In other implementations, the real-time measurements provide a monitoring and guidance function, in that measurements of parameter/s associated with tool-tissue interaction are used to monitor the progress of the insertion procedure and verify that the medical tool is following its preplanned trajectory. Such real-time monitoring obviates the need for continuous or frequent imaging throughout the insertion procedure, in order to track the tool's actual position.

In further implementations, the real-time measurements provide a safety function, i.e., measurements of parameter/s associated with tool-tissue interaction are used to alert the clinician, and preferably also automatically halt the insertion procedure, upon detecting that the medical tool has hit/ entered a forbidden area, such as a bone, a blood vessel, or the like.

It can be appreciated that in some implementations the real-time measurements may provide all of the above-mentions functions (gating, monitoring and guidance and safety) or any two-function combination thereof.

In some implementations, a force sensor is employed for measuring the forces exerted on the tool during insertion. The force profile encountered during insertion may be compared to the force profile expected from the preplanned insertion procedure. The latter is known from the arrangement and type of tissues and other body parts which the tool is expected to encounter during execution of the planned insertion path. Different force levels are encountered as the tool enters a new tissue layer, and they depend also on whether the tool is entering the patient's skin, fat tissue, muscle, or any other such characterized tissue. The expected force profile may include such features as the force levels themselves, local peaks, the spatial slopes of the measured forces, and the like, and combinations and the order of such features. The force profile can conveniently be a spatial force profile, but if the pace of the insertion procedure is predetermined, a temporal force profile can alternatively be used. Departure from this expected force profile may be indicative of departure of the tool from the preplanned insertion path. Such departure from the preplanned insertion path can thus be indicated without the need for imaging of the subject, thereby reducing the extent of any concomitant radiation exposure of the subject and of the medical staff. Further, as long as the force profile encountered during insertion matches the expected force profile, the insertion procedure can be executed without the need for continuous or frequent imaging of the subject throughout the course of the procedure.

The consequent action to be taken depends upon the extent of the departure from the expected force profile. In some implementations there are three levels which characterize the actions to be taken, depending on the extent of departure from the expected force profile.

(a) Within a limited predetermined range, up to a first threshold, meaning that the force profile is being followed within that limited range threshold, no action need be taken and the procedure is continued as planned.

(b) For a larger deviation, up to a second threshold level of deviation, it is understood that the tool is no longer following the preplanned insertion procedure sufficiently closely, but that the departure from the preplanned procedure is not sufficient to abandon the complete procedure. Instead, one or more investigative images are now generated in order to determine to what extent and in what direction departure has taken place from the preplanned path. Using this image, or these images, the insertion path is amended in order to ensure that the guided tool insertion does result in the tool reaching its intended target region of the subject, without entering en-route a forbidden area, such as a blood vessel or a bone. The expected force profile encountered by the tool can then be re-determined, from a knowledge of the type of tissues and their location expected as the tool follows the amended insertion path. The insertion can thus continue without the need for further imaging, using a comparison of the force sensor output profile with the forces expected from the amended insertion path, until the target is reached, or until another deviation from the expected force profile is encountered.

(c) If the deviation is even larger, and exceeds the second threshold level, it is assumed that the tool has deviated so far from the planned insertion procedure, that it has unintentionally hit an object such as a bone or a blood vessel, or that there is danger of damage to body parts/organs of the subject which the tool was not intended to encounter. In these circumstances, the entire insertion procedure is abandoned.

The advantage of the present methods, and of the apparatus for performing these methods, is that the level of imaging required to follow the preplanned insertion path is substantially reduced from prior art image-based insertion procedures. Use of this force guided navigation procedure is thus able to ensure accurate insertion, yet with only a fraction of the radiation otherwise required, since images are only necessary when the actual force profile deviates above a certain predetermined level from the expected force profile.

In some implementations, one or more patterns in the sensor measurements, which are indicative of the tool reaching a tissue boundary, for example, may be pre-defined. It is noted that throughout this disclosure the term "pattern" may refer to either values or behavior patterns. Thus, pre-defined patterns may be, for example, certain measured levels (e.g., force levels), slopes, local peaks, or any combination of the above.

There is thus provided in accordance with an exemplary implementation of the systems described in this disclosure, a system for controlling the insertion of a medical tool into a body of a subject, the system comprising:
(i) an insertion device configured to insert the medical tool into the body of the subject,
(ii) at least one sensor configured to measure an interaction parameter associated with the interaction between the medical tool and a bodily tissue, and
(iii) at least one processor configured:
(a) to receive measurements from the at least one sensor,
(b) to detect one or more pre-defined patterns in the measurements of the at least one sensor, and
(c) to control an operation of at least one of the insertion device and an imaging device, upon detecting at least one of said one or more pre-defined patterns in the measurements of the at least one sensor.

The at least one processor of such a system may be further configured to determine if any sensor measurements exceed a predetermined threshold. The at least one processor may be further configured to determine an actual correlation between an insertion parameter and the sensor measurements, and it may further be configured to compare said actual correlation to an expected correlation between the insertion parameter and the sensor measurements. The insertion parameter may be, for example, insertion depth or insertion time. The at least one processor may be further configured to determine said expected correlation.

In such systems, controlling an operation of at least one of an insertion device and an imaging device upon detecting said one or more pre-defined patterns in the measurements of the at least one sensor may comprise one or more of: initiating imaging of a region of interest in the body of the subject, pausing (or stopping) continuous imaging of the region of interest, continuing insertion of the medical tool into the subject's body according to at least one of a pre-planned trajectory or an adjusted trajectory, and halting the insertion of the medical tool.

Further, in such systems, the one or more pre-defined patterns in the sensor measurements may include at least one of: a level of the measured parameter, a slope, a peak or a combination thereof. The at least one sensor may comprise a force sensor, an acoustic sensor and/or any other suitable sensor.

In the case where one sensor is employed, it may be disposed on the insertion device or on the medical tool. In the case where two sensors are employed, one sensor may be disposed on the insertion device and the other sensor on the medical tool, or both may be disposed on either the insertion device or the medical tool. If more than two sensors are employed, the additional ones may be disposed as required by the system measurement preference.

There is further provided in accordance with an alternative implementation of the systems of the present disclosure, a system for controlling the insertion of a medical tool into a body of a subject, comprising:
 (i) an insertion device configured to insert the medical tool into the body of the subject,
 (ii) a force sensor configured to measure forces exerted on the medical tool during insertion into the body of the subject, and
 (iii) a processor configured:
  (a) to receive force measurements from the force sensor,
  (b) to determine an actual correlation between an insertion parameter and the force sensor measurements,
  (c) to compare said actual correlation to an expected correlation between the insertion parameter and the force sensor measurements, and
  (d) to control an operation of the insertion device based on the result of said comparison.

The at least one processor of such a system may be further configured to determine said expected correlation, which may be determined based on one or more images of a region of interest in the body of the subject and a pre-planned tool insertion trajectory. In such cases, the at least one processor may be further configured to obtain/receive said one or more images of the region of interest. Further, the at least one processor may be further configured to initiate imaging of the region of interest and/or pause or stop imaging of the region of interest in case the procedure is executed under continuous imaging. The at least one processor may be further configured to calculate said pre-planned trajectory.

In any of such systems, the forces measured by the force sensor may be one or more of axial forces and lateral forces exerted on the medical tool. The insertion parameter used in such systems for determining the actual correlation between said insertion parameter and the force measurements and comparing the actual correlation to an expected correlation may be, for example, insertion depth or insertion time.

In any of the above described systems, the at least one processor may be further configured to generate one or more graphs of the sensor measurements as a function of an insertion parameter. The insertion parameter may be insertion depth, or it may be insertion time. Finally, the at least one processor may be further configured to generate one or more of a visual, auditory and tactile feedback (e.g., alert).

Still other example implementations involve a method for controlling the insertion of a medical tool into a body of a subject, the method comprising:
 (i) inserting said medical tool into the body of the subject,
 (ii) measuring one or more interaction parameters associated with the interaction between said medical tool and a bodily tissue of said subject,
 (iii) detecting one or more pre-defined patterns in said measurements of said one or more parameters, and
 (iv) controlling an operation of at least one of an insertion device and an imaging device, upon detecting at least one of said one or more pre-defined patterns.

In such a method, the step of controlling an operation of at least one of an insertion device and an imaging device upon detecting said one or more pre-defined patterns in said measurements may comprise one or more of: initiating imaging of a region of interest in the body of the subject, pausing (or stopping) continuous imaging of the region of interest, continuing insertion of the medical tool into the subject's body according to either of a pre-planned trajectory or an adjusted trajectory, and halting the insertion of the medical tool. In some cases, such a method may comprise the step of prompting a user to initiate imaging of a region of interest in the body of the subject upon such detection. The one or parameters which the at least one processor is configured to measure in such methods may be forces exerted on said medical tool by said bodily tissue.

Alternative implementations may further involve a method for controlling the insertion of a medical tool into a body of a subject, comprising:
 (i) inserting the medical tool into the body of the subject,
 (ii) measuring forces exerted on the medical tool during insertion into the body of the subject,
 (iii) determining an actual correlation between an insertion parameter and the force measurements,
 (iv) comparing the actual correlation to an expected correlation between the insertion parameter and the force measurements, and
 (v) controlling the insertion of the medical tool into the body of the subject based on the result of the comparison.

This method may further comprise the step of determining said expected correlation, which may be based on one or more images of a region of interest in the body of the subject and the pre-planned trajectory. The method may further comprise the step of obtaining/receiving said one or more images and it may further comprise the step of determining said pre-planned trajectory.

Additionally, such methods may further include the step of determining if a deviation of said actual correlation from said expected correlation exceeds a pre-determined level. If the deviation exceeds the pre-determined level, the method may further comprise the step of halting the insertion of the medical tool, and it may further comprise the step of providing an alert upon halting the insertion of the medical tool. If the deviation does not exceed the pre-determined level, the method may further comprise the step of initiating imaging of a region of interest in the body of the subject. The imaging may be discrete, e.g., CT scans, or it may be continuous, e.g., CT fluoroscopy, such that initiating imaging may refer to reactivation of continuous imaging which was previously paused. The method may further comprise the step of adjusting the trajectory of the medical tool based on said initiated images. In such cases, the method may further comprise the step of adjusting the expected correlation between the insertion parameter and the force measurements based on said initiated images and said adjusted trajectory, and it may further comprise the step of storing the adjusted expected correlation. Following adjustment of the trajectory of the medical tool, controlling the insertion of the medical tool into the body of the subject based on the result of the comparison may comprise inserting said medical tool into the subject's body according to said adjusted trajectory.

An alternative implementation performs a method for controlling the insertion of a medical tool into a body of a subject, comprising:
(i) inserting a medical tool into the body of the subject according to a pre-planned trajectory,
(ii) measuring forces exerted on the medical tool during insertion into the body of the subject,
(iii) determining if one or more force measurements deviate from a predetermined threshold, and
(iv) halting the insertion of the medical tool, if it is determined that the one or more force measurements deviate from the predetermined threshold.

Such a method may further include the step of providing an alert if it is determined that the one or more force measurements deviate from the predetermined threshold.

Still other example implementations may involve a system for monitoring the insertion of a medical tool into a body of a subject, comprising:
(i) an insertion device configured to insert the medical tool into the body of the subject,
(ii) a force sensor configured to measure forces exerted on the medical tool during insertion into the body of the subject, and
(iii) at least one processor configured:
(a) to receive force measurements from the force sensor,
(b) to determine an actual correlation between an insertion parameter and the force sensor measurements, and
(c) to determine if the actual correlation departs from an expected correlation between the insertion parameter and the force sensor measurements.

Yet other alternative implementations may involve a method for monitoring the insertion of a medical tool into a body of a subject, comprising:
(i) measuring forces exerted on the medical tool during insertion into the body of the subject,
(ii) determining an actual correlation between an insertion parameter and the forces exerted on the medical tool during insertion into the body of the subject,
(iii) comparing the actual correlation to an expected correlation between the insertion parameter and the force measurements, and
(iv) determining if the actual correlation departs from the expected correlation.

According to yet further implementations of the methods described in the present application, there is provided a method for reducing intraoperative imaging during a medical tool insertion procedure, comprising:
(i) calculating an insertion path for said medical tool,
(ii) using said insertion path to ascertain forces expected to be encountered by said medical tool during said insertion procedure,
(iii) generating an expected force profile for said insertion procedure,
(iv) measuring the forces encountered by said medical tool as it is inserted along said insertion path,
(v) comparing said encountered forces with forces anticipated from said expected force profile, and
(vi) obtaining one or more images of a region of interest if said encountered forces deviate from the forces anticipated from said expected force profile by more than a predetermined level, such that the number of images required during said insertion procedure is reduced compared with an insertion procedure relying only on image-based navigation.

Any of the above described methods may further include the step of generating one or more graphs of the force measurements as a function of an insertion parameter. The insertion parameter may be, for example, insertion depth or insertion time.

Implementations of the system and method described hereinabove may further include any of the features described in the present disclosure, including any of the features described hereinabove in relation to other system/method implementations.

It is to be understood that although the examples used throughout this disclosure relate mainly to systems and methods for insertion of a needle into a subject's body, this is done for simplicity reasons alone, and the scope of this disclosure is not meant to be limited to insertion of a needle but is understood to include insertion of any tool intended to be inserted into a subject's body for diagnostic and/or therapeutic purposes, such as a needle, port, introducer, catheter, cannula, surgical tool, fluid delivery tool, or any other such tool.

In addition, the terms "user", "doctor", "physician", "clinician", "technician", "medical personnel" and "medical staff" are used interchangeably throughout this disclosure and they may refer to any person taking part in the performed medical procedure.

Further, it is to be understood that the terms proximal and distal as used in this disclosure have their usual meaning in the clinical arts, namely that proximal refers to the end of a device or object closest to the person or machine inserting or using the device or object and remote from the patient, while distal refers to the end of a device or object closest to the patient and remote from the person or machine inserting or using the device or object.

BRIEF DESCRIPTION OF THE DRAWINGS

Some exemplary implementations of the methods and systems of the present disclosure are described with reference to the accompanying drawings. In the drawings, like reference numbers indicate identical or substantially similar elements.

FIG. 3 shows the exemplary insertion device of FIG. 2 having a different force sensor.

DETAILED DESCRIPTION

Figure 1:
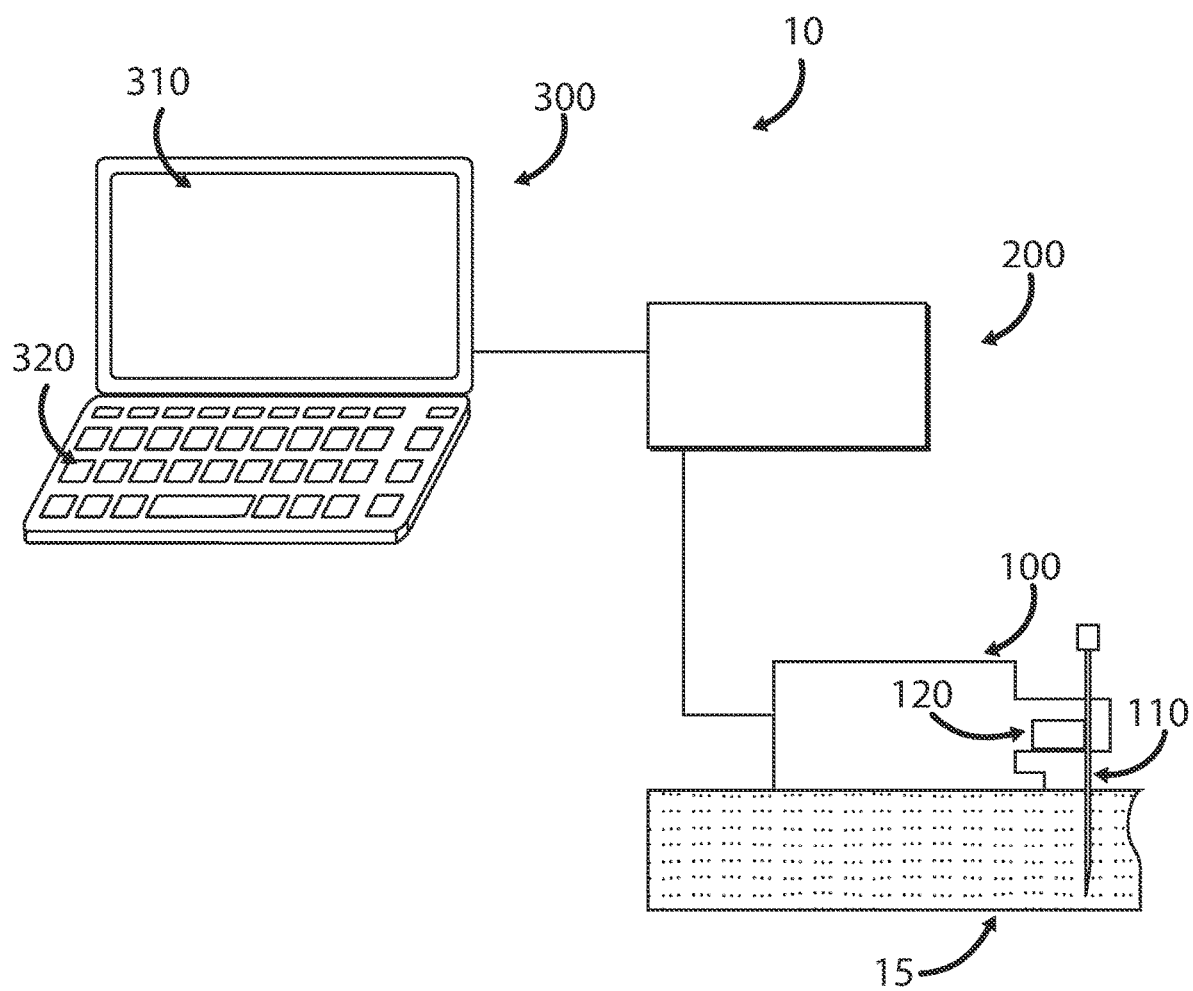
FIG. 1 shows a schematic diagram of an exemplary system for inserting a needle into the body of a subject, which includes a sensor for measuring parameter/s associated with needle-tissue interaction.

FIG. 1 shows a schematic diagram of an exemplary system 10 for inserting a medical tool such as a needle, into the body of a subject. The system includes an automated insertion device 100, such as a robot, which in some implementations may also be configured for steering the needle during its insertion into the subject's body. A needle 110 may be removably coupled to the insertion device 100, such that the insertion device 100 can be used repeatedly with new needles. In some implementations, the insertion device 100 may be configured for placement/attachment onto the subject's body 15, as shown in FIG. 1. In other implementations, the insertion device may be coupled to a dedicated arm or base connected, for example, to the patient's bed, to the gantry of an imaging system, such as a ct or MRI system, or to a cart positioned adjacent the patient's bed, as described, for example, in U.S. patent application No. U.S. Ser. No. 15/027,438 to Glozman et al, for "Needle Steering by Shaft Manipulation", and in U.S. patent application Ser. No. 15/027,439 to Glozman et al, for "Gripper for Robotic Image Guided Needle Insertion", both of which are incorporated herein by reference in their entireties.

In some implementations the insertion system 10 may include an imaging system, or it may be configured to operate in conjunction with an imaging system. The utilized imaging modality may be any one of X-ray fluoroscopy, CT, cone beam CT, CT fluoroscopy, MRI, ultrasound, or any other suitable imaging modality.

The system may further include a robot controller 200 for controlling the movement of the insertion device 100 and for steering the needle 110 towards a target, such as a lesion or a tumor, within the subject's body. The robot controller 200 may comprise one or more of a controller, motor drive/s, electrical wires, etc. The robot controller 200 may be a separate unit, as shown in FIG. 1. Alternatively, one or more components of the robot controller 200 may be embedded within the insertion device 100, and/or within a computer 300.

The insertion system 10 may further comprise a computer 300, including at least one processor (not shown) and a display 310. The computer 300 may be a personal computer (PC), a laptop, a tablet, a smartphone or any other processor-based device. The computer 300 may also include a user interface 320, which may be in the form of buttons, switches, keys, a keyboard, a computer mouse, a joystick, a touch-sensitive screen, etc. The display 310 and user interface 320 may be two separate components, or they may form together a single component, in case a touch-sensitive screen ("touch screen"), for example, is utilized.

The computer 130 may be configured, inter alia, to receive, process and visualize on the display 131, images from the imaging system (such as in DICOM format) and to calculate the optimal pathway for the needle based on input from the user, i.e., entry point, target and areas to avoid en route. In some implementations, the computer 130 may be further configured to control the steering of the needle in a closed-loop manner, generating motion commands to the insertion device 100 via the controller 120 and receiving feedback regarding the actual location of the tool, which is then used for real-time path corrections. The optimal pathway may be calculated in a two-dimensional plane or in a three-dimensional space. In some implementations, the pathway may be originally calculated in a two-dimensional plane; however, the real-time pathway corrections are executed in the three-dimensional space. Such a scenario may be due to tissue movement, for example, that prevents the planned pathway from being followed and it is also not possible to adjust the needle pathway such that it remains in the original plane.

The system 10 may further include at least one sensor 120 for measuring one or more parameters associated with needle-tissue interaction, such as a force sensor for measuring forces exerted on the needle 110 during insertion, as shown in FIGS. 2 to 4B hereinbelow, and/or an acoustic sensor (not shown), such as an ultrasonic sensor, for measuring tissue compliance. In the latter case, small oscillations may be applied whilst the needle is being inserted into the subject's body, and by measuring the resulting frequencies/amplitudes, differences in tissue compliance may be identified. Identification of such differences may further allow tissue characterization and classification, such that the physician can know what type of tissue the needle is being inserted into. The sensor 120 may be located in or on the insertion device 100 or it may be located on the needle 110 coupled to the insertion device 100. In cases where a force sensor is employed, the sensor may be adapted to measure force and/or torque about one or more axes, e.g., axial force, lateral forces, etc., and throughout this disclosure, the term "force sensor" may be used to mean either a linear force sensor, or a torque sensor, or a combination of both. Further, it can be understood that a force sensor may measure force/torque directly or it can measure other parameters, such as resistance, voltage, capacitance, or the like, which are indicative of the forces exerted on the needle.

In some implementations, the sensor 120 is connected to the computer 300 via the controller 200, as shown in FIG. 1. Alternatively, the sensor 120 may be connected directly to the computer 300. In some implementations, the sensor 120 may be connected to an amplifier (not shown) located in the insertion device 100, such that the sensor signals are amplified before they are received by the controller/computer. The computer's processor may be configured to analyze the sensor data and provide visual, auditory and/or tactile feedback. For example, the processor may be configured to generate a real-time graph of measurements taken by the sensor 120, e.g., the force/torque exerted on the needle 110, as a function of the needle insertion depth and/or as a function of the insertion time. Further, the processor may be configured to compare sensor measurements or parameters derived from the sensor's measurements, with predetermined levels or patterns, and then to control the insertion device according to the result of those comparisons.

Reference is now made to FIGS. 2-4B, which illustrate exemplary implementations of force sensors incorporated within automated insertion devices or on end effectors of such insertion devices.

Figure 2:
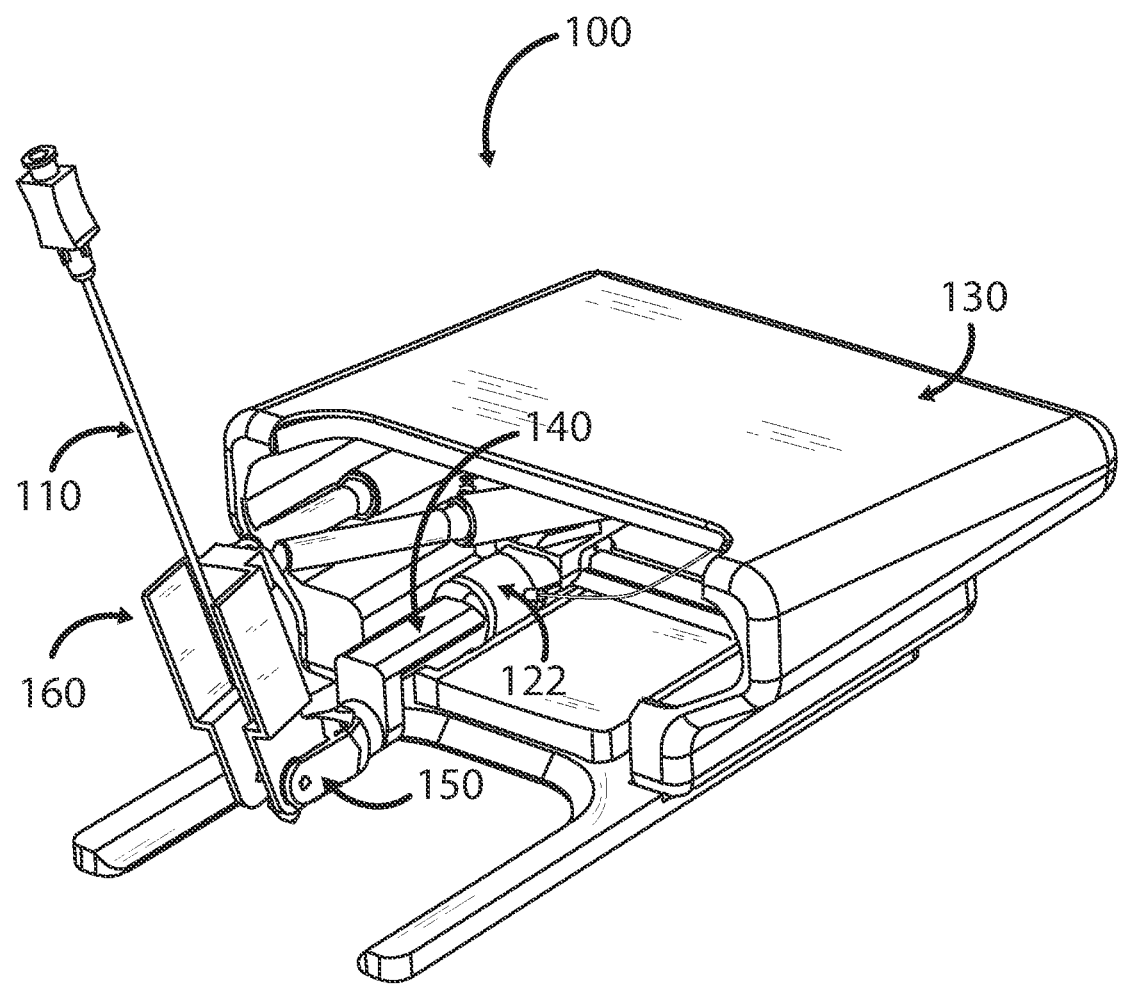
FIG. 2 shows an exemplary insertion device which includes a force sensor.

FIG. 2 shows an exemplary insertion device 100. In some implementations, the insertion device 100 may include a housing 130 configured for accommodating at least a portion of the device's movement mechanism and optionally also electronic components. The movement mechanism may include at its distal end, i.e., the end closer to the needle, a base arm 140 connected to a gimbal 150, which in turn may be connected to the device's end effector 160. In some implementations, the needle 110 may be coupled to the end effector 160 via an insertion module (not shown in FIG. 2). A force sensor 122 may be positioned on the base arm 140, and it may be configured to measure one or more of the axial and lateral forces exerted on the needle 110 by the tissue during insertion into the subject's body. In some implementations, the force sensor 122 may be a commercially available force sensor, such as Nano17 manufactured by ATI Industrial Automation of North Carolina, USA. In other implementations, the force sensor may comprise one or more strain gauges 124 positioned, for example, on the base arm 140, as shown in FIG. 3. It is to be understood that any other suitable force/torque sensor may be implemented in the systems of the present disclosure.

Figure 4A:
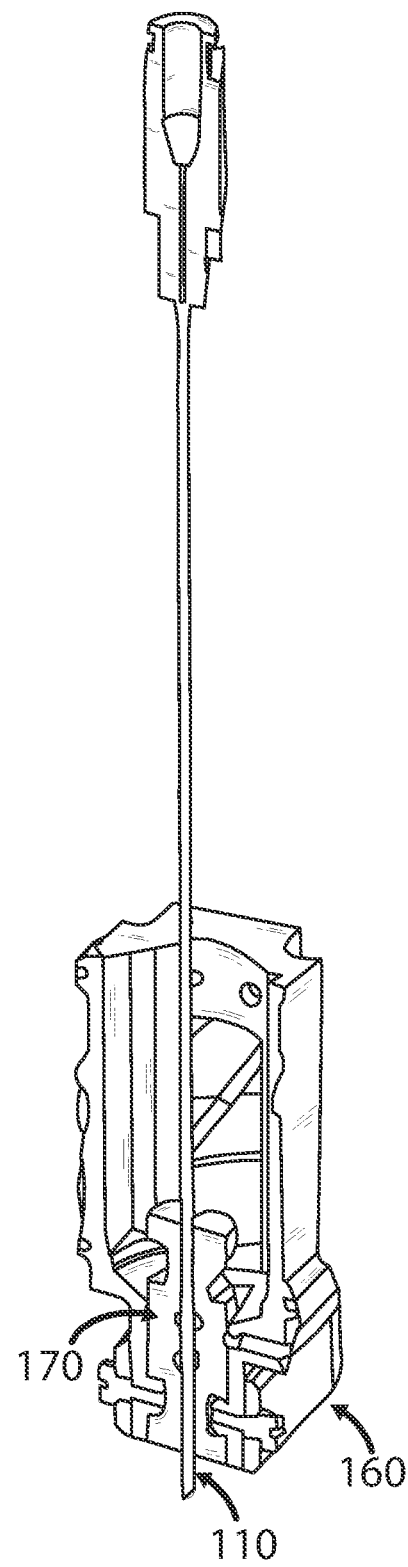
FIG. 4A shows a longitudinal cross-sectional view of an exemplary robot end effector with an insertion module and needle coupled thereto.

FIG. 4A shows a longitudinal cross-sectional view of an exemplary end effector 160 with an insertion module 170 and needle 110 coupled thereto. In some implementations, the force sensor (not shown in FIG. 4A) may be located on an inner wall of the end effector 160, or on an outer wall of the insertion module 170, such that upon coupling the insertion module 170 to the end effector 160, the force sensor is positioned between the end effector 160 and the insertion module 170, thus measuring the forces between the two, as will be shown in FIG. 4B.

Figure 4B:
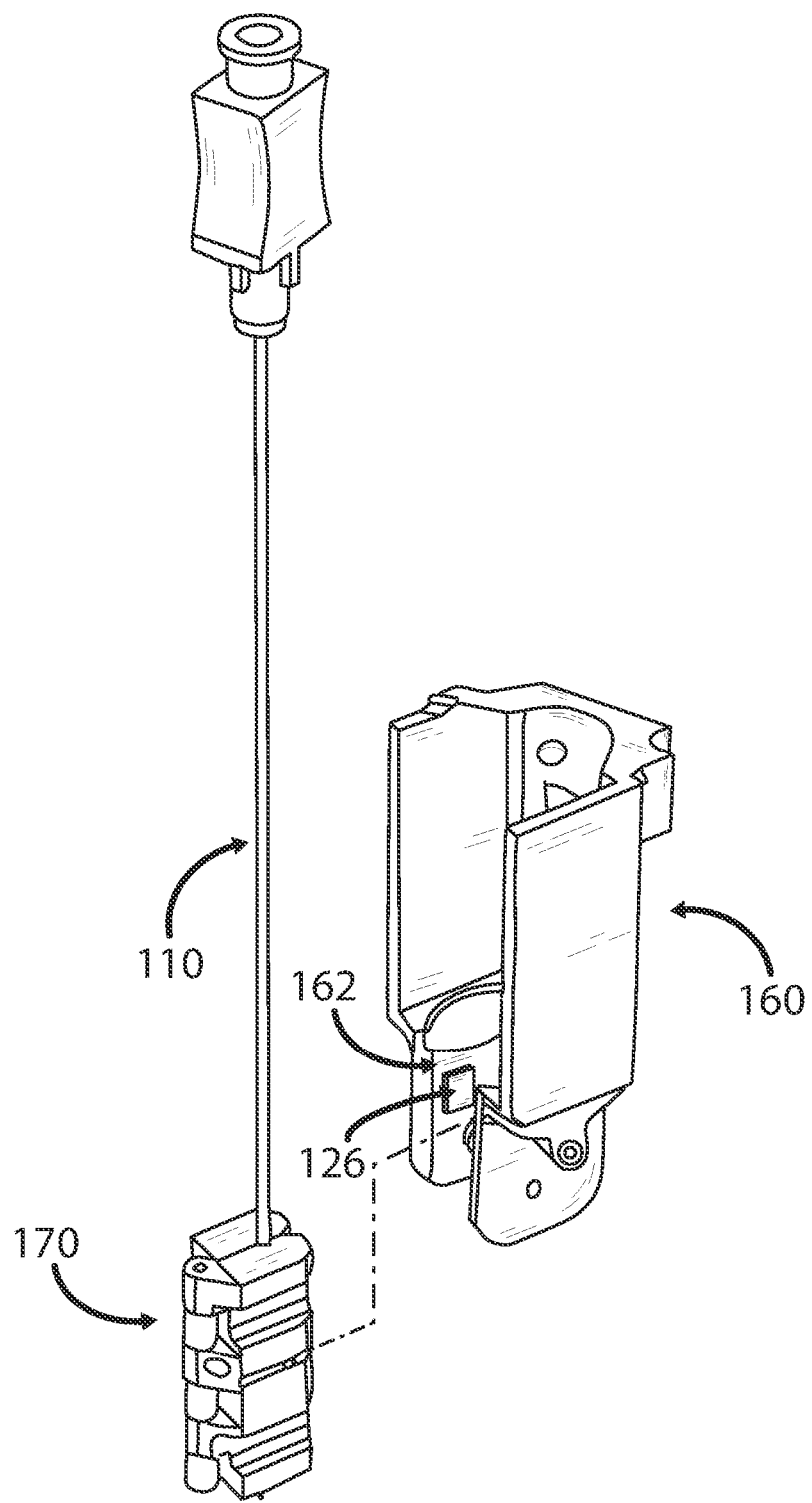
FIG. 4B shows an exploded view of the end effector with a force sensor coupled thereto, and the insertion module with the needle coupled thereto, of FIG. 4A.

FIG. 4B shows an exploded view of the exemplary end effector 160 and the insertion module 170 and needle 110 coupled thereto. Also shown, schematically, is a force sensor 126 located on an inner wall 162 of the end effector 160, such that upon coupling the insertion module 170 to the end effector 160, the force sensor 126 is positioned between the end effector 160 and the insertion module 170, and thus measures the force generated between the two. The force sensor 126 may comprise one or more strain gauges, or any other suitable force sensor.

Figure 5:
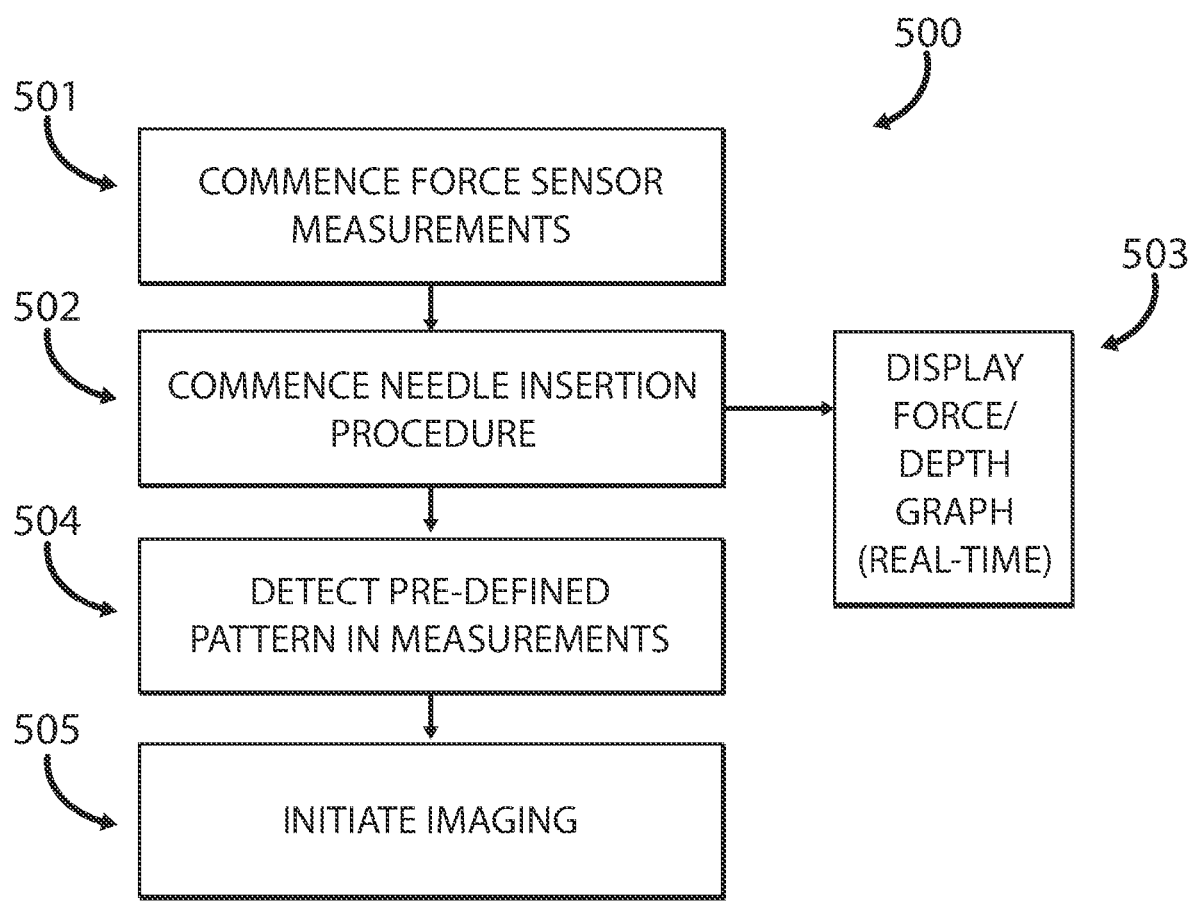
FIG. 5 is a flowchart showing the steps executed in an exemplary method of utilizing the force sensor data for initiating imaging of the region of interest.

FIG. 5 is a flowchart 500 showing the steps executed in an exemplary method based on detected force levels/patterns, of utilizing force sensor data for initiating imaging of the region of interest.

In step 501, force measurements commence. In some implementations activation of the force sensor is done by the operator/user of the insertion device. In other implementations, the force sensor is activated automatically upon activation of the insertion device. In further implementations, the force sensor may be permanently and continuously activated, such that there is no need to activate it in order for force measurements to commence.

In step 502, the needle insertion procedure commences. In some implementations, the insertion is carried out by the insertion device according to a pre-planned trajectory. Methods for planning insertion trajectories are disclosed, for example, in co-assigned International Patent Application Publication No. WO2015/132787 to M. Shochat, for "Dynamic Planning Method for Needle Insertion", which is hereby incorporated by reference in its entirety.

In step 503, a graph of the force/torque measurements as a function of the insertion depth may optionally be generated and displayed. The graph may be used to assist the physician in assessing the progress of the insertion, for example. In some implementations, a graph of the force/torque measurements as a function of the insertion time may be displayed instead of or in addition to the graph of the force/torque measurements as a function of the insertion depth. It can be appreciated that other graphs or relevant data from the force sensor may be generated and presented during the insertion process. Additional feedback from the sensor, such as alerts, may be visual, auditory and/or tactile. It can further be appreciated that such graphs/data/feedback may also be generated and presented in any of the other methods disclosed hereinbelow.

In step 504, a pre-defined pattern is detected in the measured force profile. The pre-defined pattern may be, for example, certain force levels (absolute or relative), a certain slope, a local peak in a force graph (such as the graph displayed in step 503), or any combination of the above. This pre-defined pattern may indicate that a tissue (i.e., skin, fatty tissue, muscle, etc.) boundary, or the target (e.g., tumor), has been reached. In some implementations, more than one pattern is pre-defined.

In step 505, imaging (e.g., a CT scan) is initiated. In some implementations, the imaging is carried out automatically by the system once the pre-defined pattern is detected. In other implementations, the processor/controller may alert the user once the pre-defined pattern is detected, and the user then manually initiates imaging of the region of interest. The alert may be visual, auditory, tactile, a combination thereof, or any other suitable form of alert. According to the described method, imaging of the region of interest is preferably carried out during the procedure only when a pre-defined pattern in the force measurements, which indicates reaching a tissue boundary or the target, is detected. Thus, the exposure of the patient and the medical staff to radiation during the insertion process is significantly minimized.

Figure 6:
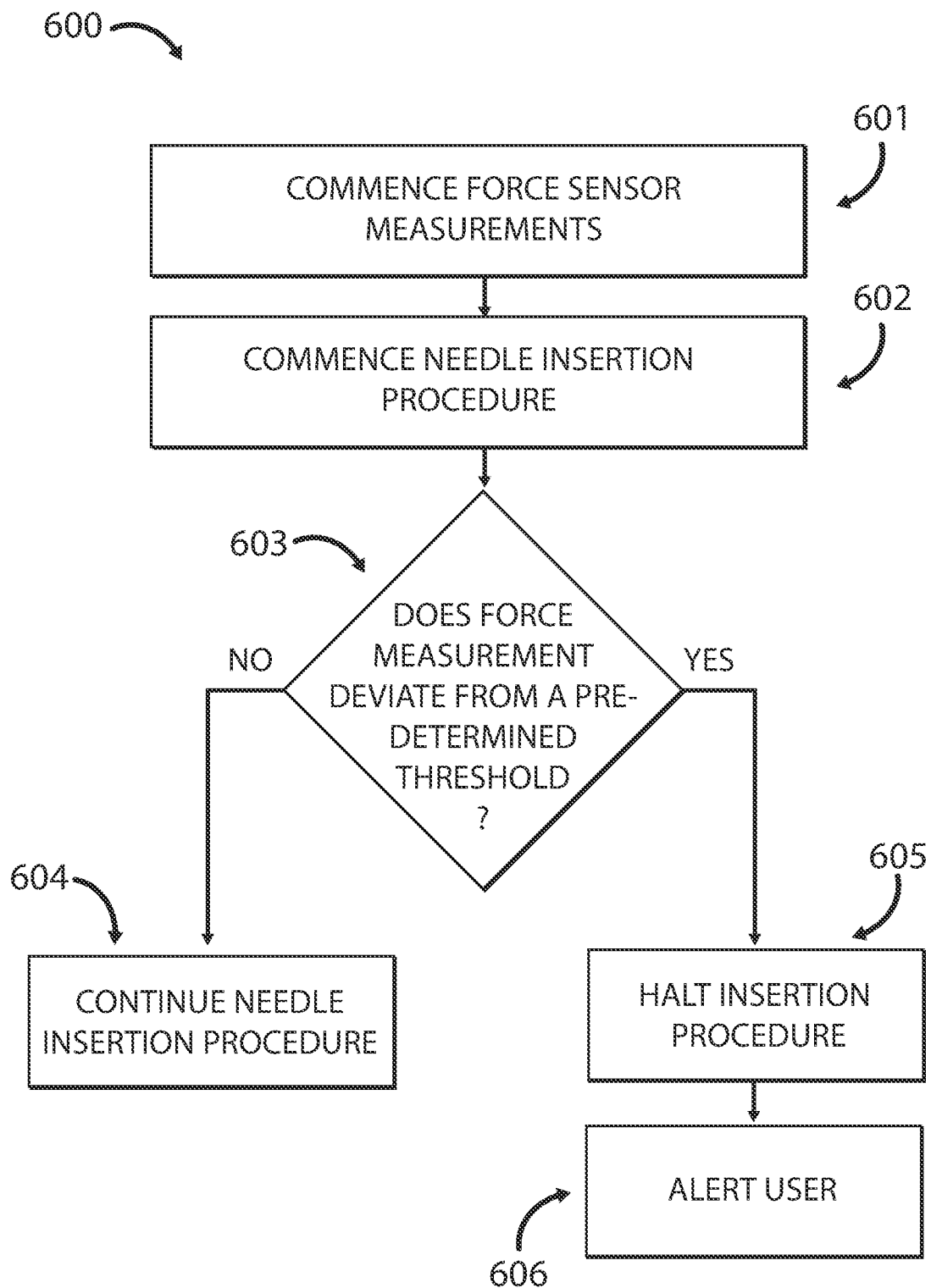
FIG. 6 is a flowchart showing the steps executed in an exemplary method of controlling the operation of an automated insertion device based on force sensor data.

FIG. 6 is a flowchart 600 showing the steps executed in the decision-making aspects of an exemplary method of controlling the operation of an automated insertion device based on force sensor data.

In step 601, force measurements commence. In some implementations activation of the force sensor is done by the operator/user of the insertion device. In other implementations, the force sensor is activated automatically upon activation of the insertion device. In further implementations, the force sensor may be permanently and continuously activated such that there is no need to actively activate it in order for force measurements to commence.

In step 602, the needle insertion procedure commences. In some implementations, the insertion is carried out by the insertion device according to a pre-planned trajectory. Methods for planning insertion trajectories are disclosed, for example, in the above referenced International Patent Application Publication No. WO2015/132787.

In step 603, the program determines if the force measurement deviates from a predetermined threshold. The threshold may be a maximum threshold or a minimum threshold, or there may be both a maximum threshold and a minimum threshold, such that there is an acceptable range of measurements. If the force measurement exceeds the predetermined maximum threshold, this may indicate that the needle has encountered an obstacle or an area which should be avoided, such as a bone or a blood vessel, which typically exert large forces on the needle. If the force measurement is lower than the minimum threshold, this may indicate that the needle has entered an undesired area, such as an organ (e.g., intestine). It can therefore be understood that the described method is of high significance for assuring patient safety. In some implementations, the predetermined threshold may be an absolute level of force measured by the force sensor. In other implementations, the threshold may be a certain pattern, such as a sudden increase/decrease in force levels, or the like.

The force measurements and comparison to the threshold may be carried out continuously throughout the insertion procedure, or they may be carried out in a discrete manner, either randomly or according to a predefined time schedule, e.g., every 50 ms, every 100 ms, or the like. In some implementations the comparison may be carried out discretely based on the insertion depth of the needle, e.g., every 1 mm, every 2 mm, or the like. If at no point during the insertion procedure does the force measurement exceed the predetermined maximum threshold, or fall below the minimum threshold, the needle insertion procedure is continued, in step 604, until the target is reached. If, however, a force measurement either exceeds or falls below respectively either the predetermined maximum or minimum threshold during the insertion procedure, then the insertion procedure is halted in step 605, and the user is alerted in step 606. In some implementations, the insertion process is halted automatically by the processor/controller and the user is alerted thereafter. In other implementations, the processor/controller may alert the user once it is determined that the force measurement has deviated from the predetermined threshold, and the user then manually stops the insertion process. The alert may be visual, auditory, tactile, a combination thereof, or any other suitable form of alert.

Figure 7:
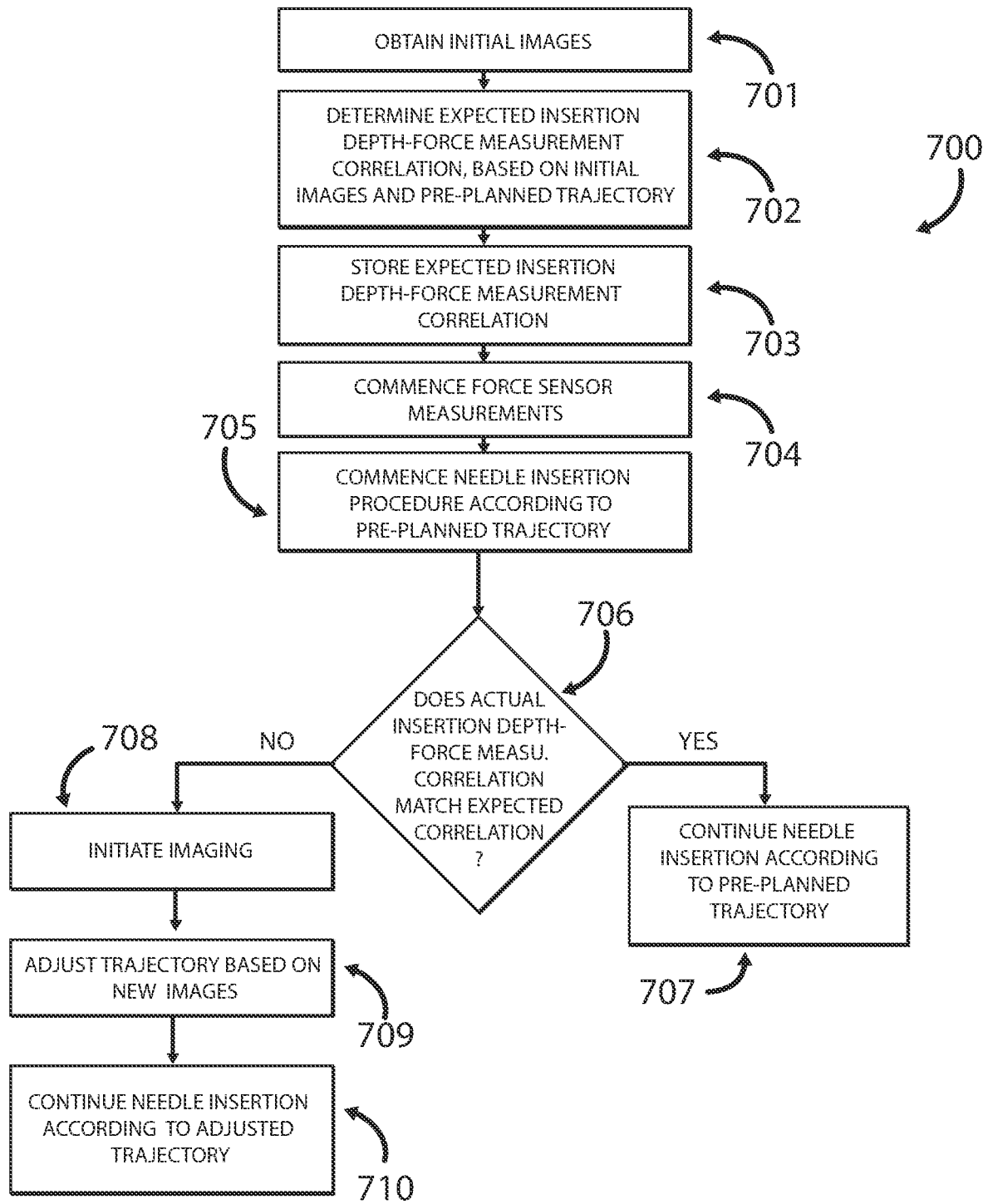
FIG. 7 is a flowchart showing the steps executed in an exemplary method of utilizing force sensor data for monitoring needle trajectory and controlling the operation of an automated insertion device based on the force sensor data.

FIG. 7 is a flowchart 700 showing the steps executed in an exemplary method of utilizing force sensor data for monitoring the trajectory of a medical tool during the insertion procedure and controlling the operation of the automated insertion device based on the force sensor data.

In step 701, at least one initial scan (e.g., CT images) of the region of interest is obtained. The image(s) may be retrieved from the imaging system in any applicable method, such as directly (i.e., an embedded system), using a communication module (i.e., transferring DICOM file(s) over a local area network), or using an external storage unit, such as a CD, DVD, USB portable drive, etc.

In step 702, the expected insertion depth-force measurement correlation for that procedure is determined, based on the initial image(s) and the planned needle trajectory. Methods for planning insertion trajectories are disclosed, for example, in the above referenced International Patent Application Publication No. WO2015/132787. In some implementations, the planned trajectory and the tissue boundaries are marked on the image(s) by the user/physician. In other implementations, they are marked automatically by the system. The expected insertion depth-force measurement correlation for that particular procedure may be calculated based on the manual markings of the user/physician, or using image processing, for example. Typically, data obtained from previous insertion procedures and/or experiments demonstrating insertion depth-force measurement correlation, is used in determining the expected correlation. In some implementations, an expected elapsed insertion time to force measurement correlation may be determined instead or in addition to the expected insertion depth to force measurement correlation, and this possibility is understood to be included whenever reference is made hereinbelow to the insertion depth-force measurement correlation.

In step 703, the expected insertion depth-force measurement correlation is stored. It is to be noted that steps 701 to 703 are generally performed pre-operatively, i.e., in the planning stage of the procedure.

In step 704, force measurements commence. In some implementations activation of the force sensor is done actively by the operator/user of the insertion device. In other implementations, the force sensor is activated automatically upon activation of the insertion device. Alternatively, the force sensor may be permanently and continuously activated such that there is no need to actively activate it in order for force measurements to commence.

In step 705, the needle insertion procedure commences according to the pre-planned trajectory.

In step 706, the actual insertion depth-force measurement correlation is compared to the expected insertion depth-force measurement correlation and it is determined if the actual correlation matches the expected correlation. It is to be understood that certain tolerances may be pre-defined as acceptable. In some implementations, the actual insertion depth may be determined using internal tracking/measurement systems. For example, the insertion system may include an encoder coupled to the motor (or other actuator) which operates the insertion mechanism, and encoder readings and/or their derivatives (e.g., number of motor rotations) are translated to needle translation, and thus needle insertion depth can be derived. In other implementations, the actual insertion depth may be determined using external tracking systems, such as electromagnetic tracking systems or optical measurement systems, or any other suitable tracking system. The actual force measurements are obtained from the force sensor.

The comparison between the actual correlation and the expected correlation may be, for example, of values, slopes, peaks, certain patterns or any combination thereof. Research has shown, for example, that after the needle comes into contact with the tissue boundary, but before it penetrates the tissue, the tissue boundary deflects under the influence of the load applied by the needle tip. As the needle displaces the tissue boundary, the load at the needlepoint increases, as do the stresses in the tissue surrounding the contact area. Once these stresses exceed a certain critical value, a crack will be initiated in the tissue and the needle will start to penetrate the tissue. When a thin membrane is punctured, the amount of energy stored during the boundary displacement phase is often so large that rupture occurs. This results in a (relatively large) drop in force as the accumulated strain energy is used to extend the crack. Rupture continues until the strain energy levels become low enough for the crack extension to proceed in a stable manner (see the above-referenced article "Needle-tissue interaction forces—A survey of experimental data", pages 667-669). Thus, an exemplary expected pattern may be a peak in the force levels preceded by a non-linear increase in force and followed by a drop in the force levels. The comparison may be carried out continuously throughout the insertion procedure, or it may be carried out in a discrete manner, either randomly or according to a predefined time schedule, e.g., every 50 ms, every 100 ms, or the like. In some implementations the comparison may be carried out discretely based on the insertion depth of the needle, e.g., every 1 mm, every 2 mm, or the like.

If it is determined that the actual insertion depth-force measurement correlation matches the expected insertion depth-force measurement correlation then, in step 708, the insertion procedure is continued according to the pre-planned trajectory, with no need to pause the procedure and image the region of interest in order to determine the needle's actual position, since the actual correlation matching the expected correlation indicates that the needle is successfully following its pre-planned trajectory and it is at its expected position.

If it is determined, however, that the actual insertion depth-force measurement correlation does not match the expected insertion depth-force measurement correlation then, in step 708, imaging is initiated, in order to determine the needle's actual position.

In step 709, the needle trajectory is adjusted based on the new image/s and the actual needle position as derived from the new image/s.

In step 710, the insertion procedure is continued according to the adjusted trajectory.

Figure 8:
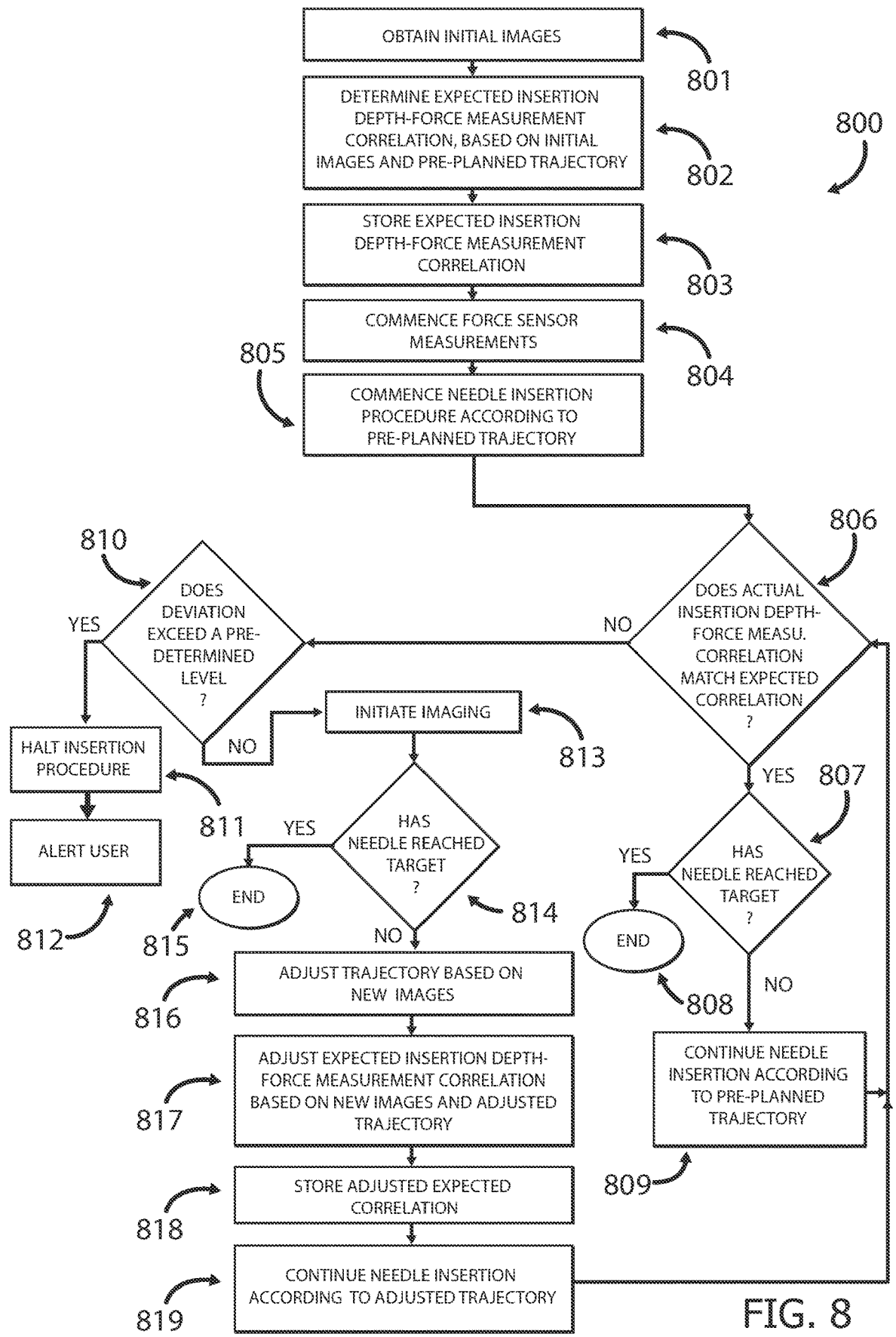
FIG. 8 is a flowchart showing the steps executed in another exemplary method of utilizing force sensor data for monitoring needle trajectory and controlling the operation of an automated insertion device based on the force sensor data.

FIG. 8 is a flowchart 800 showing the steps executed in another exemplary method of utilizing force sensor data for monitoring the trajectory of a medical tool such as a needle during the insertion procedure and controlling the operation of the automated insertion device based on the force sensor data.

In step 801, at least one initial scan (e.g., CT image/s) of the region of interest is obtained. The image/s may be retrieved from the imaging system in any applicable method, such as directly (i.e., an embedded system), using a communication module (i.e., transferring DICOM file(s) over a local area network), or using an external storage unit, such as a CD, DVD, USB portable drive.

In step 802, the expected insertion depth-force measurement correlation for that procedure is determined, based on the initial image/s and the preplanned needle trajectory, as described hereinabove with regard to step 702 in FIG. 7.

In step 803, the expected insertion depth-force measurement correlation is stored.

In step 804, force measurements are commenced.

In step 805, the needle insertion procedure commences according to the pre-planned trajectory.

In step 806, the actual insertion depth-force measurement correlation is compared to the expected insertion depth-force measurement correlation and it is determined if the actual correlation matches the expected correlation. The actual insertion depth and the actual force measurements are determined as described hereinabove with regard to step 706 in FIG. 7.

If it is determined that the actual insertion depth-force measurement correlation matches the expected insertion depth-force measurement correlation then, in step 807, it is determined if the needle has reached the target (e.g., tumor). Such a determination may be derived from the depth measurements and/or the force measurements and/or a combination thereof. For example, reaching the target may be determined based on force levels typical for the target of the specific procedure, or from typical force patterns. A graph of force measurements as a function of insertion depth (and/or insertion time), may be generated in real time during the procedure and it may be used for determining if the target has been reached. If the target has been reached, then, in step 808, the procedure comes to an end. If, however, the target has not yet been reached, then, in step 809, the needle insertion procedure continues according to the pre-planned needle trajectory, as the match between the actual correlation and the expected correlation indicates that the needle is at its expected position. Thus, no additional imaging is required in order to verify the needle's position, and the amount of radiation exposure to the patient and medical staff during such procedures is significantly reduced. The process then returns to step 806, where the actual insertion depth-force measurement correlation is again compared (continuously or discretely) to the expected insertion depth-force measurement correlation. The process may include several iterations, until the needle reaches the target.

In some implementations, the insertion procedure is executed under continuous imaging, such as using cone-beam CT or CT fluoroscopy. In such cases, if it is determined that the actual insertion depth-force measurement correlation matches the expected correlation, and that the target has not yet been reached, the continuous imaging may be paused, or stopped entirely, as the insertion procedure continues according to the pre-planned needle trajectory, since the match between the actual correlation and the expected correlation indicates that the needle is successfully following its pre-planned trajectory. The continuous imaging may be paused/stopped automatically, manually by the user, or semi-automatically, e.g., the system software may prompt the user to select between continuing the continuous imaging or pausing/stopping it and the user then manually selects between the two options. In case the continuous imaging is paused, it may remain paused until it is determined at a later point during the procedure that the actual insertion depth-force measurement correlation does not match the expected correlation and the deviation does not exceed a pre-determined level, as will be explained below. If the result of every following comparison between the actual correlation and the expected correlation, until the target is reached, that the actual correlation matches the expected correlation, then the continuous imaging may remain paused/stopped until the completion of the procedure. Returning now to step 807, if it is determined that the actual insertion depth-force measurement correlation does not match the expected insertion depth-force measurement correlation then, in step 810 it is determined if the deviation of the actual correlation from the expected correlation exceeds a predetermined level. The deviation may be in terms of a force level at a specific insertion depth (too high or too low), or reaching a certain force level sooner/later than expected (depth-wise in case of an insertion depth-force measurement correlation, or time-wise in case of an insertion time-force measurement correlation).

If it is determined that the difference between the actual insertion depth-force measurement correlation and the expected correlation exceeds the predetermined level, this may indicate that the needle has hit an obstacle, for example, or that the needle has deviated significantly from its pre-planned trajectory. Thus, the insertion process is halted in step 811, and the user is alerted, in step 812. In some implementations, the insertion process is halted automatically by the processor/controller and the user is alerted thereafter. In other implementations, the processor/controller may alert the user once it is determined that the difference between the actual insertion depth-force measurement correlation and the expected correlation exceeds the predetermined level, and the user then manually stops the insertion process. The alert may be visual, auditory, tactile, a combination thereof, or any other suitable form of alert. In some implementations, the processor/controller may not only alert the user that the deviation between the actual correlation and the expected correlation exceeds the predetermined level, but it may further prompt the user to stop the insertion process.

If it is determined in step 810 that the difference between the actual insertion depth-force measurement correlation and the expected correlation does not exceed the predetermined level, then, in step 813, imaging is initiated, in order to determine the needle's actual position. In some implementations imaging initiation may be automatic, whereas in other implementations the system software may prompt the user to initiate imaging. In cases in which the insertion procedure is executed under continuous imaging, such as using cone-beam CT or CT fluoroscopy, and the continuous imaging is already active when step 813 is reached, then nothing is to be done at step 813, and step 812 will be followed by step 814. If the continuous imaging has been previously paused, i.e., following a determination at the previous iteration that the actual insertion depth-force measurement correlation matches the expected correlation, then at step 813 the continuous imaging may be resumed, either automatically by the system software, manually by the user or semi-automatically, e.g., the system software may prompt the user to manually reactivate the continuous imaging.

In step 814, it is determined, based on the new image/s, if the needle has reached the target (e.g., tumor). If the target has been reached, then the procedure comes to an end, in step 815. If, however, the target has not yet been reached, then, in step 816, the needle trajectory is adjusted, based on the new image/s and the actual needle position as derived from the new image/s.

In step 817, the expected insertion depth-force measurement correlation is adjusted based on the new image/s and the adjusted trajectory. The new correlation may be calculated based on manual markings done by the user/physician of the arrangement and type of tissues and other body parts which the needle is expected to encounter during the adjusted insertion trajectory, and/or using image processing.

In step 818, the adjusted expected insertion depth-force measurement correlation is stored.

In step 819, the needle insertion procedure is continued according to the adjusted trajectory, and the process returns to step 806, where the actual insertion depth-force measurement correlation is now compared (continuously or discretely) to the adjusted expected insertion depth-force measurement correlation. The process may include several iterations, until the needle reaches the target.

Although particular implementations have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the disclosure as defined by the claims. For example, the logic flows depicted in the accompanying figures and described herein do not require the particular order shown, or sequential order, to achieve desirable results. Other aspects, advantages, and modifications are considered to be within the scope of the following claims. The claims presented are representative of the implementations and features disclosed herein. Other unclaimed implementations and features are also contemplated. Accordingly, other implementations are within the scope of the following claims.

The invention claimed is:

1. A system for monitoring insertion of a medical tool through a tissue of a subject, the system comprising:
    a force sensor configured to measure forces exerted on the medical tool during insertion into the tissue of the subject; and
    at least one processor configured to:
        receive force measurements from the force sensor;
        determine a real-time correlation between an insertion parameter and the force measurements;
        compare the real-time correlation to an expected correlation between the insertion parameter and the force measurements by comparing one or more pre-defined patterns in the real-time and expected correlations, the one or more pre-defined patterns being indicative of the medical tool reaching a boundary between tissue layers;
        determine if a deviation of the real-time correlation from the expected correlation exceeds a pre-determined threshold; wherein if the deviation of the real-time correlation from said expected correlation does not exceed the pre-determined threshold, initiate one or more real time images of a region of interest in the subject;
        adjust the trajectory of the medical tool based on the one or more real-time images of a region of interest in a body of the subject; and
        adjust the expected correlation between the insertion parameter and the force measurements based on at least one of the one or more images and the adjusted trajectory.

2. The system of claim 1, wherein the at least one processor is configured to determine the expected correlation based on one or more initial images of the region of interest and a pre-planned trajectory.

3. The system of claim 2, wherein the at least one processor is configured to calculate the pre-planned trajectory.

4. The system of claim 2, further comprising an insertion device configured to insert the medical tool into the tissue of the subject, and wherein the at least one processor is configured to control the insertion of the medical tool by the insertion device, the insertion being according to at least one of the pre-planned trajectory and the adjusted trajectory.

5. The system of claim 1, wherein the one or more pre-defined patterns comprise at least one of: a force level, a peak in the force measurements, a sudden increase in the force measurements, a sudden decrease in the force measurements, and a slope of a generated graph of the force measurements as a function of the insertion parameter.

6. The system of claim 1, wherein the insertion parameter is one or more of insertion depth and insertion time.

7. The system of claim 6, further comprising at least one of an internal tracking system and an external tracking system, wherein the at least one processor is configured to determine a real-time insertion depth using the at least one of the internal tracking system and the external tracking system.

8. The system of claim 1, wherein the force sensor is disposed on one or more of an insertion device and the medical tool.

9. A method for monitoring insertion of a medical tool through a tissue of a subject, the method comprising:
    measuring at least one interaction parameter associated with an interaction between the medical tool and the tissue of the subject;
    determining an actual correlation between an insertion parameter and the measurements of the at least one interaction parameter; and
    comparing the actual correlation to an expected correlation between the insertion parameter and the measurements of the at least one interaction parameter, to determine if the actual correlation deviates from the expected correlation;
    wherein if it is determined that the actual correlation deviates from the expected correlation, determining if the deviation exceeds a pre-determined threshold;
    wherein if it is determined that the deviation does not exceed the pre-determined threshold, initiating one or more images of a region of interest in the subject and adjusting the expected correlation based on the one or more images of a region of interest in a body of the subject.

10. The method of claim 9, wherein the at least one interaction parameter comprises forces exerted on the medical tool during insertion through the tissue of the subject.

11. The method of claim 9, wherein comparing the actual correlation to an expected correlation comprises comparing one or more pre-defined patterns in the actual and expected correlations.

12. The method of claim 11, wherein the one or more pre-defined patterns are indicative of the medical tool reaching a boundary between tissue layers.

13. The method of claim 9, wherein the insertion parameter comprises one or more of insertion depth and insertion time.

14. The method of claim 9, further comprising determining an actual position of the medical tool within the tissue of the subject based on the one or more images.

15. The method of claim 9, further comprising adjusting the trajectory of the medical tool based on the one or more images and controlling insertion of the medical tool through the tissue of the subject according to the adjusted trajectory.

16. The method of claim 9, comprising halting the insertion of the medical tool and generating an alert, if it is determined that the deviation exceeds the pre-determined threshold.

\* \* \* \* \*